US00PP15691P2

(12) United States Plant Patent
Smith

(10) Patent No.: US PP15,691 P2
(45) Date of Patent: Mar. 22, 2005

(54) ***ASTER* PLANT NAMED 'YOPUFF'**

(50) Latin Name: *Aster hybrida*
Varietal Denomination: Yopuff

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/818,349

(22) Filed: Apr. 5, 2004

(51) Int. Cl.[7] ..... A01H 5/00

(52) U.S. Cl. ..... Plt./355

(58) Field of Search ..... Plt./355

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Aster* plant named 'Yopuff', characterized by its uniform, outwardly spreading and mounded plant habit; freely branching growth habit; dark green-colored foliage; uniform flowering habit; natural flowering season around September $10^{th}$; daisy-type inflorescences with white-colored ray florets; and good garden performance.

2 Drawing Sheets

Botanical classification/cultivar designation: *Aster hybrida* cultivar Yopuff.

BACKGROUND OF THE INVENTION

The present Invention relates to a new and distinct cultivar of *Aster* plant, botanically known as *Aster hybrida* and hereinafter referred to by the name 'Yopuff'.

The new *Aster* is a product of a planned breeding program conducted by the Inventor in Alva, Fla. The objective of the program is to create or discover new potted *Aster* cultivars that have a uniform plant growth habit, good vigor and strong branching habit, numerous inflorescences, desirable inflorescence form and floret colors, uniform flowering response and good postproduction longevity.

The new *Aster* originated from an open-pollination made by the Inventor in Feburary, 2001, in Alva, Fla., of a proprietary seedling selection of *Aster hybrida* identified as code number AS0527, not patented, as the female, or seed, parent with a an unknown *Aster* selection, not patented, as the male, or pollen, parent. The new *Aster* was discovered and selected by the Inventor in March, 2002, as a single flowering plant from within the resulting progeny of the stated open-pollination grown in a controlled environment in Alva, Fla.

The selection of this plant was based on its uniform plant growth habit, good vigor and strong branching habit, numerous inflorescences, desirable inflorescence form and floret colors, uniform flowering response and good postproduction longevity.

Asexual reproduction of the new *Aster* by vegetative tip cuttings was first conducted in Alva, Fla. in May, 2002. Asexual reproduction by cuttings has shown that the unique features of this new *Aster* are stable and reproduced true to type in successive generations.

SUMMARY OF THE INVENTION

The cultivar Yopuff has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yopuff'. These characteristics in combination distinguish 'Yopuff' as a new and distinct cultivar of *Aster:*

1. Uniform, outwardly spreading and mounded plant habit.
2. Freely branching growth habit.
3. Dark green-colored foliage.
4. Uniform flowering habit.
5. Natural flowering season around September $10^{th}$.
6. Daisy-type inflorescences with white-colored ray florets.
7. Good garden performance.

Plants of the new *Aster* can be compared to plants of the female parent selection. In side-by-side comparisons conducted in Alva, Fla., plants of the new *Aster* differed from plants of the female parent selection in the following characteristics:

1. Plants of the new *Aster* flowered more uniformly than plants of the female parent selection.
2. Plants of the new *Aster* flowered three days earlier than plants of the female parent selection under natural season conditions.
3. Inflorescences of plants of the new *Aster* and the female parent selection differed in ray floret color as plants of the female parent selection had pink-colored ray florets.

Plants of the new *Aster* can be compared to plants of the cultivar White Swan, not patented. In side-by-side comparisons conducted in Alva, Fla., plants of the new *Aster* differed from plants of the cultivar White Swan in the following characteristics:

1. Plants of the new *Aster* were stronger and more rain tolerant than plants of the cultivar White Swan.
2. Plants of the new *Aster* were smaller than plants of the cultivar White Swan.
3. Plants of the new *Aster* flowered about five days later than plants of the cultivar White Swan under natural season conditions.

4. Plants of the new *Aster* had slightly smaller inflorescences than plants of the cultivar White Swan.
5. Inflorescences of plants of the new *Aster* were longer-lasting than inflorescences of plants of the cultivar White Swan.

Plants of the new *Aster* can also be compared to plants of the cultivar Monte Casino, not patented. In side-by-side comparisons conducted in Alva, Fla., plants of the new *Aster* differed from plants of the cultivar Monte Casino in the following characteristics:

1. Plants of the new *Aster* were smaller and more densely mounded than plants of the cultivar Monte Casino.
2. Leaves of plants of the new *Aster* were larger and darker green in color than leaves of plants of the cultivar Monte Casino.
3. Plants of the new *Aster* flowered about 2.5 weeks earlier than plants of the cultivar Monte Casino under natural season conditions.
4. Plants of the new *Aster* had larger inflorescences and more ray florets per inflorescence than plants of the cultivar Monte Casino.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster*.

The photograph on the first sheet comprises a side perspective view of a typical flowering plant of 'Yopuff' grown in a container.

The photograph on the second sheet comprises a close-up view of typical inflorescences of 'Yopuff'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the winter in Alva, Fla., in a polyethylene-covered greenhouse and under conditions which approximate those generally used in commercial potted *Aster* production. During the production of these plants, day temperatures were about 25° C. and night temperatures were about 18° C. Unrooted cuttings were directly stuck in 15-cm containers, exposed to long day/short night conditions, and pinched several times. At the time of the final pinch, photoinductive short day/long night treatments were initiated.

Botanical classification: *Aster hybrida* cultivar Yopuff.

Parentage:

*Female, or seed, parent.*—Proprietary seedling selection of *Aster hybrida* identified as code number AS0527, not patented.

*Male, or pollen, parent.*—Unknown *Aster hybrida* selection, not patented.

Propagation:

*Type.*—Terminal vegetative cuttings.

*Time to initiate roots.*—About one week at 21° C.

*Time to produce a rooted cutting.*—About 16 to 19 days at 21° C.

*Root description.*—Fine, fibrous; white, close to 155D.

*Rooting habit.*—Freely branching.

Plant description:

*Appearance.*—Daisy-type potted *Aster*. Upright with lateral branches outwardly spreading; inverted triangle with uniformly mounded crown. Strong and freely branching growth habit with lateral branches developing at every node when pinched (removal of terminal apices); dense and full plants. Moderately vigorous.

*Plant height.*—About 21 cm.

*Plant width.*—About 28 cm.

*Lateral branches.*—Length: About 20 cm. Diameter: About 1.5 mm. Internode length: About 9 mm. Strength: Strong. Texture: Smooth, glabrous. Color: Close to 147A.

*Foliage description.*—Arrangement: Alternate; simple; sessile. Length: About 6.9 cm. Width: About 1 cm. Shape: Linear. Apex: Acute. Base: Attenuate. Margin: Entire to serrate. Texture, upper and lower surfaces: Smooth, glabrous. Color: Developing and fully expanded foliage, upper surface: 147A. Developing and fully expanded foliage, lower surface: 147B. Venation, upper surface: 147A. Venation, lower surface: 147B.

Inflorescence description:

*Appearance.*—Daisy-type inflorescence form with linear-shaped ray florets. Inflorescences terminal and axillary. Disk and ray florets develop acropetally on a capitulum. Inflorescences not fragrant.

*Flowering response.*—Under natural conditions, plants flower on September $10^{th}$ in Alva, Fla. Uniform flowering habit.

*Inflorescence longevity.*—Inflorescences maintain good color and substance for about one to two weeks on the plant.

*Quantity of inflorescences.*—About seven open inflorescences per lateral branch.

*Inflorescence bud.*—Height: About 4 mm. Diameter: About 3 mm. Shape: Spherical. Color: Close to 147A.

*Inflorescence diameter.*—About 3.3 cm.

*Inflorescence height.*—About 1.2 cm.

*Diameter of disc.*—About 8 mm.

*Receptacle diameter.*—About 1.75 mm.

*Ray florets.*—Shape: Linear. Orientation: Initially upright, then about 90° from vertical. Aspect: Straight, mostly flat. Length: About 1.6 cm. Corolla tube length: About 2 mm. Width: About 2 mm. Apex: Acute. Base: Fused into a corolla tube. Margin: Entire. Texture: Smooth, glabrous, satiny. Number of ray florets per inflorescence: About 47 arranged in two or three whorls. Color: When opening and fully opened, upper surface: Close to 155D. When opening and fully opened, lower surface: Close to 155D.

*Disc florets.*—Arrangement: Massed at center of receptacle. Shape: Tubular, elongated. Apex: Five-pointed. Length: About 6 mm. Diameter, apex: About 1.5 mm. Diameter, base: About 1 mm. Number of disc florets per inflorescence: About 47. Color: Apex: Close to 155D. Mid-section: Close to 144D. Base: Close to 155D.

*Phyllaries.*—Quantity per inflorescence: About 38. Length: About 4 mm. Width: Less than 1 mm. Shape: Ligulate. Apex: Acute. Base: Truncate, fused. Margin: Entire. Texture, upper surface: Waxy, smooth.

Texture, lower surface: Smooth. Color, upper and lower surfaces: Close to 147A.

*Peduncles.*—Length: First peduncle: About 2.5 cm. Fourth peduncle: About 3.5 cm. Diameter: Less than 1 mm. Angle to vertical: About 45° from vertical. Strength: Strong, flexible. Texture: Smooth, glabrous. Color: 147A.

*Reproductive organs.*—Androecium: Anther color: Close to 11D. Pollen amount: None observed. Gynoecium: Style color: Close to 11D. Stigma color: Close to 11D.

*Seed/fruit.*—Seed and fruit production has not been observed.

Disease/pest resistance: Resistance to pathogens and pests common to *Asters* has not been observed on plants grown under commercial greenhouse conditions.

Garden performance: Plants of the new *Aster* have been observed to be rain and wind tolerant and to tolerate temperatures from 0 to more than 38° C.

It is claimed:

1. A new and distinct cultivar of *Aster* plant named 'Yopuff', as illustrated and described.

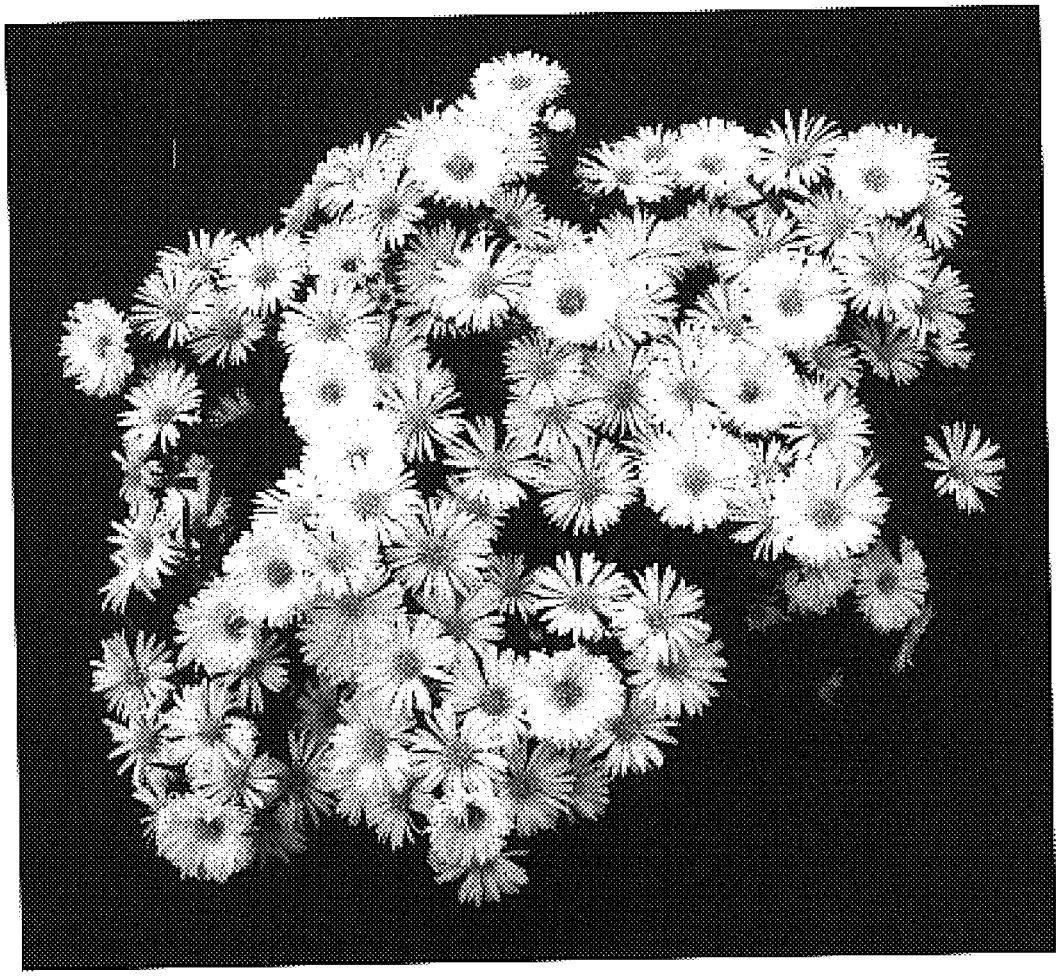

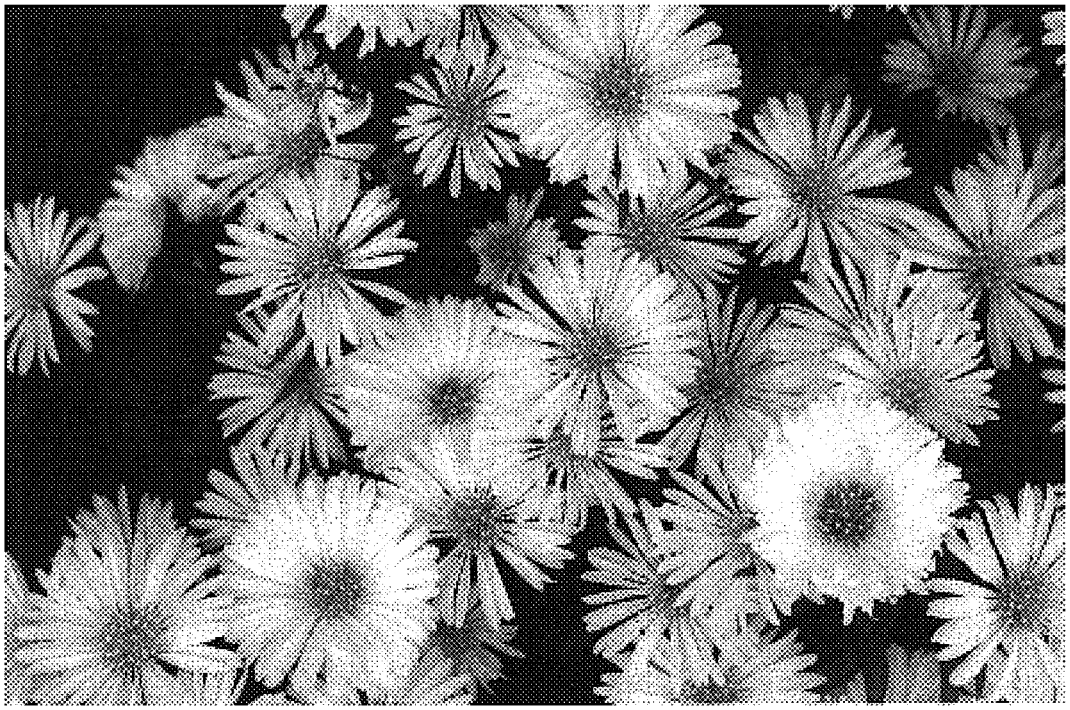

* * * * *